United States Patent [19]

Shaw

[11] Patent Number: 4,515,957
[45] Date of Patent: May 7, 1985

[54] PURIFICATION OF MERCAPTOBENZOTHIAZOLE

[75] Inventor: Chong-Kuang Shaw, Broadview Heights, Ohio

[73] Assignee: The B. F. Goodrich Company, Akron, Ohio

[21] Appl. No.: 410,170

[22] Filed: Aug. 20, 1982

[51] Int. Cl.³ .......................................... C07D 277/72
[52] U.S. Cl. ..................................................... 548/177
[58] Field of Search ................................. 548/165, 177

[56] References Cited

U.S. PATENT DOCUMENTS

| | | | |
|---|---|---|---|
| 2,137,820 | 11/1938 | Williams | 548/177 |
| 2,631,153 | 3/1953 | Paul | 548/177 |
| 2,730,528 | 1/1956 | Weyker | 548/177 |
| 3,804,846 | 4/1974 | Okamoto | 548/177 |
| 4,371,698 | 2/1983 | Alicot | 548/177 |

*Primary Examiner*—Robert Gerstl
*Attorney, Agent, or Firm*—George A. Kap; Alan A. Csontos

[57] ABSTRACT

Crude MBT is purified and substantially decolorized by treating same with an alkaline solution to form an MBT salt solution, measuring pH of the salt solution when adding the alkaline solution until an abrupt rise in pH is observed and stopping addition of the alkaline solution in response thereto, treating the salt solution with a solvent to extract solvent-soluble impurities, oxidizing the salt solution by introducing oxygen into an enclosed vessel containing the salt solution and vigorously agitating the solution until oxygen uptake essentially stops, diluting the salt solution with water, filtering the salt solution to remove precipitated impurities, and concentrating the solution.

12 Claims, No Drawings

PURIFICATION OF MERCAPTOBENZOTHIAZOLE

BACKGROUND OF THE INVENTION

Mercaptobenzothiazole (MBT) can be prepared by reacting aniline, carbon disulfide, and sulfur under elevated pressure and at an elevated temperature. At the end of this reaction, the crude reaction mass is discharged into water and MBT is extracted with a dilute alkali metal hydroxide solution whereby MBT is solubilized as an alkali metal salt. U.S. Pat. No. 1,631,871 discloses basic process for making MBT.

MBT is useful as a starting material for the production of thiazole derivatives that can be used as vulcanization accelerators. Also, MBT with ethylene glycol can be used as an anticorrosion agent.

Crude MBT is contaminated with various intermediates, unreacted materials, and by-products such as benzothiazole, anilinobenzothioazole, thiocarbanilide, and others, as well as unreacted aniline and sulfur. It is also contaminated with a resinous tarry substance having unknown composition and structure.

A gamut of purification procedures have been proposed in the past for purifying MBT. The Paul U.S. Pat. No. 2,631,153 discloses aeration of the aqueous solution of the alkali metal salt of MBT whereby MBT of improved purity can be obtained. It is disclosed in the Paul patent that during aeration, color of the alkali metal MBT solution gradually changes from dark red to orange or yellow, indicating completion of the aeration step. In the example of this patent, the sodium MBT solution was aerated for 2 hours at 60° C. and then was precipitated.

The Scherhag U.S. Pat. No. 3,770,759 also relates to purification of MBT. This patent discloses a purification process that includes the steps of dissolving the crude melt of MBT in an organic solvent, extracting MBT with a dilute alkali metal hydroxide solution, and precipitating MBT with an acid. The disadvantage of this process resides in the treatment of crude MBT melt with a solvent as opposed to water and the subsequent problems of recovering or controlling the escape of the solvent vapors.

The Sagawa U.S. Pat. No. 3,904,638 also relates to a process for purifying MBT that is obtained by reacting aniline, carbon disulfide, and sulfur. Here, crude MBT is dispersed in an aromatic solvent, the resulting dispersion is filtered to retain particles of MBT which particles are dissolved in an aqueous caustic alkali solution and the solution is then filtered to remove insoluble contaminants. The resulting solution can be used as such in the production of thiazole derivatives or the solution can be acidified with an inorganic acid to obtain solid MBT. The disadvantage of this process resides in the fact that MBT is soluble to some extent in the aromatic hydrocarbon, see Table I, as a result of which, 5% to 10% of MBT can thus be lost.

The Okamoto U.S. Pat. No. 3,804,846 achieves purification of MBT by dissolving crude MBT in an aqueous alkaline solution, reacting the resulting solution with an oxidizing agent under aeration and while being heated, admixing carbon powder and coagulating the oxidation products on the carbon powders suspended in the solution, and separating the carbon powder from the solution whereby products of oxidation are removed therefrom. Examples of suitable oxidizing agents include hydrogen peroxide, sodium or potassium chlorate, sodium or potassium hypochlorite, ammonium perchlorate, and the like.

SUMMARY OF THE INVENTION

This invention relates to purification and removal of color components of crude MBT by adding to a reactor water, molten crude MBT, and aqueous alkali metal hydroxide solution, with agitation, whereby an alkali salt of MBT is made which is water-soluble; measuring pH of the solution as the alkali is added during which time an abrupt rise in pH takes place, and stopping addition of the alkali in response to the abrupt rise in pH; treating the resulting alkali metal MBT solution with a solvent to remove solvent-soluble impurities therefrom; oxidizing certain impurities in the solution by introducing oxygen into the headspace of a closed vessel containing the salt solution and vigorously agitating the solution until oxygen-uptake essentially ceases and the impurities drop out; optionally, diluting the alkali metal MBT solution with water; filtering the alkali metal MBT solution to remove any impurities that precipitate as a result of the dilution step; and concentrating the solution by heating under vacuum.

DETAILED DESCRIPTION OF THE INVENTION

This invention relates to purification of MBT and to the removal or neutralization of color components therefrom in order to obtain a pure and a relatively colorless MBT or an alkali metal salt thereof in solution. As used herein, MBT refers specifically to 2-mercaptobenzothiazole.

Unlike the Scherhag U.S. Pat. No. 3,770,759, purification of crude MBT pursuant to this invention is accomplished by initially feeding to an agitated reactor the following materials: water, molten crude MBT, and an alkali metal hydroxide. In this respect, purification of MBT is more analogous to the procedures disclosed by other patents that issued prior to the Scherhag patent.

Amount of water pumped to the reactor can vary from 3 to 20, preferably 5 to 10 volumes per 1 volume of crude MBT and amount of alkali metal hydroxide should be sufficient to convert all of the water-insoluble MBT to water-soluble alkali metal salt of MBT, such as sodium MBT. Quantitatively, amount of alkali metal hydroxide should be closely controlled to provide a small excess over the stoichiometric amount. Usually, 50% sodium hydroxide solution is used for this purpose. The crude MBT is dispersed in the reactor in the form of small solid particles which are rendered soluble by reaction with the alkali metal hydroxide. Although the alkali metal salt of MBT is water-soluble, there are many contaminants that remain in solid form dispersed in the liquid which hereinafter, will be referred to as a dilute crude MBT salt solution containing about 10 to 35% MBT by weight. The crude MBT salt solution can be pumped from the reactor to a feed tank for storage.

The crude MBT salt solution is then extracted with a solvent to solubilize most of the solid and liquid impurities which are removed with the solvent. When the solvent is mixed with the crude MBT salt solution, a two-phase system is formed, the upper phase being the solvent containing therein solubilized impurities. In practice, however, the crude MBT salt solution can be taken from the feed tank and pumped through a column where the solvent is passed countercurrently to the crude MBT salt solution, with the dilute purified solution being extracted from the bottom and the solvent is extracted from the top of the column. The crude MBT salt solution, after solvent extraction, can be pumped to a storage tank. Solvent extraction is generally effective in removing about 95% or more of impurities.

Suitable solvents are those that can extract most of the impurities in the crude MBT salt solution. Examples of such impurities include aniline, benzothiazole, sulfur, anilinobenzothiazole, carbanilide, etc. Such solvents are liquid at room temperature and have boiling points in the range of about 30° to 200° C. under atmospheric pressure. Specific examples thereof include toluene, benzene, cresol, octylbenzene, and xylene. Also suitable are certain substituted aromatic hydrocarbons such as chlorobenzene and nitrobenzene, and other halogenated aliphatic solvents such as carbon tetrachloride and methylene dichloride and chloroform. Amount of the solvent can vary from about 0.5 to 10 parts by volume, preferably 1 to 5 parts by volume per 1 volume of the crude MBT salt solution.

From the storage tank, the solvent-extracted purified MBT salt solution is pumped to a purge tank equipped with an agitator and aeration nozzles. Oxygen under pressure is admitted from the bottom of the purge tank and allowed to pass through the solution. Oxygen treatment or oxygenation enhances precipitation of color bodies in the solution and thus results in a purer and more color-free solution. Studies have indicated that the purified MBT salt solution has a certain oxygen uptake capacity, depending on many variables, such as the amount and the type of impurities still present in the solution. In a preferred embodiment, oxygenation is continued until the oxygen uptake capacity of the solution is satisified.

Oxygenation can also be accomplished in another manner which is preferred due to a fraction of time that is required compared to oxygenation described above. In this embodiment, the purified MBT salt solution is pumped to a tank equipped with agitation means, the tank headspace is evacuated, and the tank is pressurized with oxygen. Pressure in the tank can be on the order of 100 to 200 psi, however, in a practical sense, pressure is limited by the pressure that the tank can withstand. Since oxygen absorbtion by the solution is facilitated at higher pressures, it is, therefore, preferred to pressurize with oxygen at higher pressures. This step is carried out by filling the tank with the MBT salt solution to 70-80% of its capacity, evacuating the headspace, and then introducing oxygen into the headspace. Agitation is very important in this embodiment and must be vigorous enough to cause the solution to absorb oxygen as quickly as possible. With adequate agitation, oxygen uptake is completed when the pressure in the vessel drops to a relatively constant value. Whereas the prior art talks of aeration in terms of hours, oxygenation at elevated pressure can be accomplished in less than one hour and generally in a fraction of an hour, such as a quarter of an hour.

An optional feature that further facilitates purification and removal of color contaminants is the step of diluting the MBT salt solution with water with agitation for a period of about 5 minutes to 2 hours until color bodies drop out. Agitation can be done with aeration. This procedure can be carried out in a separate vessel which has sufficient capacity to dilute one volume of the MBT salt solution with up to about 5 volumes of cold water, preferably one-half to two volumes of water. The dilution step is resorted to in the case of MBT salt solutions which have relatively high concentration of impurities, especially sulfur. Following dilution, the resulting solution is filtered to remove any residual solid contaminants and then concentrated to the desired degree, preferably by stripping under vacuum. The concentrated MBT salt solution should be 99%+pure MBT, have a Gardner color of #10 or less, and alkali metal hydroxide concentration of less than 0.5%.

Certain features of the MBT purification treatment described above will now be discussed in greater detail since they present novel and unobvious subject matter when considered in the context of known prior art. These features include the treatment of the crude MBT melt with a caustic solution and pressurized oxygenation of the MBT salt solution in a closed vessel.

It appears that the oxygen absorbing species are responsible for most of the color or impurities in the MBT salt solution. It is speculated that these species are sulfide or polysulfide anions which are converted into water-soluble forms by caustic from sulfur and sulfide and polysulfide intermediates. Based on this information, the attention given to caustic treatment and oxygenation steps becomes apparent.

In reference to the oxygenation experiments, apparatus was set up to measure consumption of oxygen by the crude MBT salt solution. The apparatus consisted of a flask into which the solution sample was placed, a buret, and a source of oxygen under pressure. The flask was provided with agitation means and a piece of tubing was connected thereto. One end of the buret was connected by means of a 3-way stopcock to the tubing whereas the other end was connected to a water reservoir that was open to the atmosphere. The connection between the buret and the reservoir was made by means of flexible tubing. The oxygen source was also connected to the tubing by means of a 3-way stopcock.

In operation, a solution sample was placed into the flask and the buret was filled with water to the top to displace all air therein. The flask was degassed by connecting it to a source of vacuum and then filled with pure oxygen. The buret was then filled with pure oxygen and the pressure in the buret and the flask was balanced by raising or lowering the water reservoir against atmospheric pressure, at which time, volume of oxygen in the buret was recorded as of time zero. The reaction between the contaminants and oxygen was initiated by vigorous agitation of the solution sample. Oxygen consumption was indicated by the rising level of water in the buret and the consumed oxygen volume was read after balancing the water level in the water reservoir and the water level in the buret.

Progress of oxygenation was followed by the oxygen volume in the buret against time and provided the total volume of oxygen requirement. One sample, for instance, consumed 1.27 ml of oxygen per gram of solution and another sample, 1.43 ml of oxygen per gram of solution, under ambient conditions. Oxygen consumption is directly related to purity of solution, i.e., the more oxygen uptake the less pure was the solution. This procedure, therefore, is also useful in determining relative purity of solutions.

The experiments have shown that a rapid phase of oxygen uptake is followed by a very slow rate of uptake, which indicated a finite oxygen requirement. This also indicated that the MBT salt was not being oxidized, at least not at the same rate as the impurities. Although MBT disulfide was present, amounts thereof were erratic from sample to sample and it is believed that its presence was due to trace amount of iron in the solution. Another observation that was made was that highly alkaline MBT salt solutions containing excess caustic, appeared to be more susceptible to MBT disulfide formation.

The experiments have also shown that color reduction of the solution is correlated with the volume of oxygen consumed by the solution. When time is plotted against oxygen consumption, the result is a relatively uniform uptake of oxygen over an initial period of about two hours which is followed by rapid flattening of the curve generally indicating completion of the oxidation of the impurities. Upon continuation of the oxidizing treatment, the impurities start to drop out.

The role of oxygen as a reactant has been conclusively established by the experiments and the need to increase oxygen uptake by the MBT salt solution to a maximum is self evident. Since the reaction of a gas with a liquid requires good contact, agitation has been recognized as a vital factor. For instance, it has been observed that different stirring rates directly affect the rate of oxygen consumption. When maximum agitation is provided, a steady, constant rate of oxygen consumption takes place. The criterion, therefore, for adequate agitation is the relatively constant rate of oxygen consumption at least initially during the first 1 to 2 hours of treatment. Since oxygen concentration in the solution is the key to achieving a maximum reaction rate, experiments were carried out to determine the extent of improvement provided by the use of oxygen under pressure. This was done by carrying out experiments in suitable vessels where oxygen was admitted under pressure. The results have demonstrated that high pressure oxygenation produces dramatic results. In instances when oxygen pressure was about 100 psig, oxidation procedure was less than one-half hour, generally completed in about 10 minutes with the pressure in the headspace dropping about 10%.

High pressure oxygenation must be carried out in suitable pressure vessels that can withstand high pressures. Oxygen pressure can vary anywhere from just above atmospheric to the highest pressure that a vessel can withstand. Generally speaking, high pressure oxygenation can be carried out at pressures ranging from about 50 psig to about 500 psig and more likely, about 100 to 200 psig. Consumption of oxygen can be followed by reading the pressure in the vessel which drops as more oxygen is taken up by the solution, provided there is adequate agitation. Consumption of oxygen is satisfied if the pressure in the vessel becomes substantially constant following an initial drop.

In addition to oxygen, other oxidizing agents were tried without success, however. Inorganic oxidizing agents, such as bleach (NaOCl) and iodine solution, caused formation of MBT disulfide, an undesirable solid contaminant. Hydrogen peroxide was found to be effective in removing some color but it also caused formation of MBT disulfide. Metallic salts such as ferric chloride and copper acetate, formed metal complexes with the sodium salt of MBT and precipitated out of the solution.

The purification process described herein, therefore, includes the steps of measuring the oxygen uptake over a period of time to ascertain that oxygen requirement of the MBT salt solution is satisfied and that the impurities are oxygenated and converted to a precipitate that drops out of the solution. Color reduction can also be used as an indication of sufficient oxygen uptake. Based on experimental data, color reduction of 1 to 6 units on the Gardner color scale can be achieved by oxygenation which, therefore, can be used as an indication that the oxidizing reaction has been completed. More specifically, an improvement of about 2 to 5 units on the Gardner color scale can be achieved by oxygenating the MBT salt solution until its oxygen consumption drops off substantially or entirely from the initial high rate.

Treatment of the crude MBT melt with a caustic solution must also be done with care since purity of MBT can be adversely affected. It has been determined that using excess amount of caustic in the preparation of the MBT salt has detrimental effects on the quality of certain derivatives prepared from the MBT salt which are useful as accelerators in curing of rubber and related materials. In fact, the quality of certain MBT salt derivatives was found to be inversely proportional to the amount of excess caustic used in making the MBT salt. Furthermore, these observations were found to correlate directly with the sulfur concentration in the MBT salt solution. This is consonant with the fact that the reaction of sulfur with caustic is a slower reaction than the reaction of MBT with caustic. Therefore, if caustic is present in an amount exceeding the stoichiometric amount, sulfur is consumed or reacted with caustic mostly after all of the MBT is converted to the salt and if there is a sufficient excess of caustic, all of the sulfur in the crude MBT will be consumed by the caustic. This, of course, is undesirable since the preponderance of color bodies are sulfur and sulfur compounds.

In addition to dissolution of sulfur into the MBT salt solution or reaction thereof with excess caustic, it was also discovered that aniline was also dissolved into the MBT salt solution generally in proportion to the excess caustic present. This was surprising because the opposite was expected since the increased alkalinity of the MBT salt solution should have decreased the aniline solubility.

Amount of caustic used in making the MBT salt solution also affects oxygen consumption in the oxidizing step. Data has shown that only a small volume of oxygen is consumed by the MBT salt solution when a stoichiometric amount of caustic is used. Addition of a 10% excess caustic caused increased oxygen consumption which further increased on further additions of 20% and 30% excess caustic. In the cases of increased excess caustic, oxygen consumption continued at a slower rate and the solution changed to deep red color. More importantly, it was found that the color impurities were not removable by solvent extraction.

A definite correlation was found to exist between excess caustic with oxygen consumption by the MBT salt solution. A correlation was also established between pH of the solution and excess caustic that is characteristic of the reaction of a weak acid and a strong base. A plot of pH of the solution against amount of caustic used showed a long flat curve due to the formation of a buffer solution followed by an abrupt jump in pH when the equivalent point was passed. More specifically, a plot of pH against the volume of caustic added during preparation of about 35% sodium salt of MBT, showed a change in pH from about 7 to about 10, at room temperature, on addition of a small amount of up to about 10% of a 50% caustic solution, followed by a relatively long flat curve until the equivalent point was reached, at which time, pH abruptly increased from slightly above 11 to above 13, or about 2 pH units. At about pH of 13, excess caustic used was about 1%. The pH continued to rise gradually with an increase in excess caustic. At 10% excess caustic, pH was about 13.5 and at 30% excess caustic, pH was about 14.

The abrupt increase in the pH of the MBT salt solution following the long buffering stage is used to control amount of excess caustic that is added to the solution. Since the use of a small excess of caustic is necessary to recover all of MBT, it is desirable to keep the excess to a minimum, such as 5% or less, preferably about 1% excess over and above the stoichiometric amount. The abrupt increase in pH marks the end point where all of MBT is converted to the salt. To keep excess caustic to a minimum, a pH meter is provided in the reactor into which water, crude MBT melt and caustic are added. In anticipation of the end point, addition of caustic can be reduced in order not to overshoot the objective of 5% or less of excess caustic. The end point on a plot of pH versus volume of caustic is defined as the mid point on the line indicating the abrupt increase in pH. Therefore, if it is anticipated that the end point will be at a pH of about 12, addition of caustic can be slowed at pH of about 10 or 11 and then the progress of pH increase is closely monitored until the abrupt increase takes place, at which time, addition of caustic is stopped.

As is well known, pH is temperature dependent and it also depends on other factors such as concentration of solution, and level and type of impurities present. If it is not known where the end point might be, it would be prudent to take a small sample of the crude MBT and add caustic thereto to obtain an approximate end point. Such a procedure would be time saving since reduction in caustic addition could be more closely controlled.

Therefore, another novel feature in the process for purifying MBT resides in measuring pH of the MBT salt solution and monitoring progress thereof during addition of caustic thereto and stopping addition of caustic when the end point is reached, or at any other point, for that matter. As already described, the end point is generally marked by an abrupt rise in pH of at least one quarter, and more likely about a couple of pH units during addition of about 5% or less, preferably 3% or less of an alkali metal hydroxide. The known prior art certainly discloses making MBT salt with caustic and some of the salt solutions might have been taken to the end point and only a small excess of caustic was obtained. However, the prior art does not appear to have recognized the deletereous nature of a large excess of caustic, such as above about 1%, and therefore, steps were not taken to minimize the damaging affect thereof.

The following examples are provided for illustrative purposes and may include particular features of the invention. The examples, however, should not be construed as limiting the invention since many variations thereof are possible without departing from the spirit or scope thereof. The percentages and parts given are on weight basis, unless otherwise stated.

In the following examples, crude MBT was used that was prepared at high temperature and high pressure by reacting aniline, sulfur and carbon disulfide. The crude MBT had the following composition in weight percent:

| | | |
|---|---|---|
| | MBT | 87.4% |
| | aniline | 0.3% |
| | benzothiazole | 5.6% |
| | 2-anilinobenzothiazole | 1.1% |
| | sulfur | 1.0% |
| | thiocarbanilide | 0.5% |
| | other by-products | 4.1% |

-continued

| | |
|---|---|
| | 100.0% |

EXAMPLE I

This example demonstrates the relative ineffectiveness of a 2-hour air purge that is disclosed by the Paul U.S. Pat. No. 2,631,153.

Crude MBT in amount of 100 parts by weight was placed in a vessel containing 22 parts of sodium hydroxide in 960 parts of water maintained at 60° C. The mixture in the vessel was vigorously agitated to mix the ingredients and then was purged with air for two hours using two purge lines at opposite locations in the vessel in order to provide a uniform dispersion of air through the mixture. After removing the insoluble material by filtration, the filtrate was acidified with 75 parts by volume of 9N sulfuric acid. The precipitated MBT was removed by filtration, washed three times with 1000 volumes of water, and dried in a vacuum oven at 70° C. The MBT that was obtained was in the form of yellow powder weighing 82.9 parts, melted at 173°–181° C., and had a purity of 97.0%. The yield on recovery was 94.9%.

EXAMPLE 2

Crude MBT in amount of 275 parts was placed in a vessel containing 510 parts of water. The slurry was mixed with a mechanical agitator while 240 parts of a 20% sodium hydroxide solution was added rapidly. Temperature of the solution was maintained at 50° C. and its alkalinity was monitored with a pH meter. The solution reached a constant pH of 9.75 when almost all of the sodium hydroxide was reacted. Additional caustic was added at a slower rate until abrupt rise in pH to 10.1 was maintained for 20 minutes. What was happening here was that an abrupt rise to pH of 10.1 would take place but the pH would drop with time. Addition of sodium hydroxide was continued until pH of 10.1 stabilized. During this time, additional 69 parts of 20% sodium hydroxide solution was added, for a total of 309 parts. Amount of excess sodium hydroxide was about 6%.

The resulting solution was thoroughly mixed and thus extracted three times each with 400 parts by volume of toluene and after extraction, it contained about 30% MBT and was of a brown color which corresponded to 12 on the Gardner color scale. The solution was then purged with air for 16 hours while being agitated and filtered to remove solid precipitate to yield a solution that was a 9 on the Gardner color scale. To further purify the solution, it was diluted with 800 volume parts of water and agitated for two hours in order to precipitate additional impurities. On filtering out the solid precipitate, the solution was concentrated to about 44% MBT, the color of which was 9 on the Gardner scale.

To isolate MBT, the concentrated solution was diluted with 2000 volume parts of water, and acidified with 9N sulfuric acid whereby MBT precipitated out and was recovered. The solid MBT precipitate was washed three times with water (each time with 1000 volume parts), filtered and dried in a vacuum oven. The product, weighing 238.2 parts, melted at 179.0°–182.0° C. and had a purity of 99.5%, as determined by a titration procedure. Product yield or recovery was 99.1%.

EXAMPLE 3

Procedure of Example 2 was repeated except that the 20% sodium hydroxide solution was added until a pH of 11.5 was reached at 50° C., which required a total of 334 parts of the caustic solution. Amount of excess sodium hydroxide was about 10%. The solution was extracted with toluene in the same manner and color of the solution after extraction was 14 on the Gardner scale as compared to 12 in Example 2. Air purging for 16 hours was followed by filtration of solid precipitate which yielded a solution having a color of 12 on the Gardner scale. Dilution of the solution with 800 parts of water and filtration thereof to remove precipitated matter resulted in a solution that had a Gardner 13 color upon concentration to about 44% MBT whereas color of the corresponding color of the Example 2 color was 9.

Following procedure of Example 2, MBT was isolated after neutralization with sulfuric acid as a yellow powder weighing 235.8 parts and melting at 174.5°–181.0° C., indicating purity of 98.5%. Product yield was 98.1%.

Examples 2 and 3 demonstrate the effect of increased excess caustic on purity and color of the solutions. The two examples are same with the exception that whereas amount of excess caustic in Example 2 was about 6%, the corresponding amount in Example 3 was about 10%. For this reason, Gardner color of Example 2 solution after toluene extraction was 12 whereas it was 14 in the corresponding solution of Example 3. A difference of 2 units on the Gardner color scale is considered to be a quantum or a very large difference. The improved color of Example 2 solution carried through the processing steps. For instance, Gardner color of Example 2 solution was 9 after the 16-hour air purge whereas the corresponding Example 3 solution had a Gardner 12 color. After concentration, Gardner color of Example 2 solution was 9 whereas that of the corresponding Example 3 solution as 13. The tremendous difference of 4 Gardner points is apparently attributable to the difference in the excess caustic employed while treating crude MBT.

Since purity is directly related to color of a solution, it is not surpising that purity of the concentrated Example 2 solution is higher than purity of the concentrated Example 3 solution. Although the difference is 1.4%, i.e., 99.5% v. 98.1%, it should be understood that once high purity is reached, fractional improvements are difficult to obtain.

EXAMPLE 4

This example demonstrates the concept of oxidizing the crude MBT solution in an autoclave with air.

To an autoclave was charged 800 parts of sodium MBT solution containing 30% MBT that was prepared pursuant to the procedure of Example 1 to the point before air purge. At this point, the autoclave was about 80% full of the solution. The autoclave was pressurized to 100 psig with compressed air at room temperature, then sealed and agitated. When the pressure dropped to about 80 psig in the autoclave, which indicated complete consumption of available oxygen, the autoclave was vented. Fresh compressed air was charged to 100 psig, and the autoclave was again agitated. This process was repeated until no more uptake of oxygen was experienced. A total of 65 minutes of reaction time was required and total pressure drop during this time was 25 psi. The reaction time was the time that air or pure oxygen under pressure in the autoclave was in contact with the solution while the solution was agitated to promote oxidation of the impurities therein. The total pressure drop was the difference between the initial pressure of 100 psig to which the autoclave was pressurized to the lowest pressure attained in the autoclave.

After filtering, the solution was neutralized, yielding 237.7 parts of MBT. The product melted at 176°–181° C. and had a purity of 97.5%. Yield on recovery was 98.9%.

EXAMPLE 5

The procedure of Example 4 was repeated except that pure oxygen was used instead of compressed air. A total pressure drop of 22 psi was noted in 27 minutes of reaction time to completion. After filtering and neutralization, 238.2 parts of MBT was obtained melting at 176°–181° C. with a purity of 97.8%. Yield on recovery was 99.1%.

EXAMPLE 6

The procedure of Example 4 was repeated and the air-oxidized solution was then diluted with two volumes of water and agitated for one hour. After filtering, the solution was neutralized yielding 236.9 parts of MBT melting at 178.5°–182.0° C. with a purity of 99.0%. Yield on recovery was 98.5%.

EXAMPLE 7

The procedure of Example 5 was repeated except that the oxygen-treated solution was diluted with two volumes of water and agitated for one hour to coagulate the impurities. After removing the precipitated impurities, the solution was neutralized. The recovered MBT weighed 237.9 parts and had a melting point of 179°–182° C. and a purity of 99.3%. Yield on recovery was 99.0%.

EXAMPLE 8

This example shows that solvent extraction alone will not yield good quality MBT.

The procedure of Example 2 was repeated to the completion of toluene extraction. The solution was then diluted with two volumes of water, filtered and neutralized. MBT in amount of 239.0 parts was recovered melting at 173°–181° C. with a purity of 97.5%. Yield on recovery was 99.8%.

I claim:

1. In a process for purification of crude 2-mercaptobenzothiazole (MBT) which comprises dissolving crude MBT in an aqueous alkali metal hydroxide solution in a reactor by adding the alkaline solution to the crude MBT, and agitating contents of the reactor until essentially all MBT is converted to the MBT salt, the improvement comprising measuring pH of the salt solution when addition of the alkaline solution is made during which time an abrupt rise in pH takes place that follows a period of gradual pH increase, and stopping addition of the alkaline solution in response to the abrupt rise in pH in order to limit addition of the excess alkali metal hydroxide to about 5% or less.

2. Process of claim 1 including the step of slowing addition of the alkaline solution before the abrupt rise in pH is reached to minimize addition of excess alkali to the solution, the abrupt rise being characterized by a rise of at least one-quarter of a pH point during addition of less than about 3% of the alkali.

3. Process of claim 2 wherein MBT is prepared by reacting aniline, carbon disulfide, and sulfur at a high temperature and under an elevated pressure, wherein the salt solution is treated with a solvent that solubilizes certain of the impurities in the salt solution and the salt solution is separated from the solvent having dissolved therein the impurities, and wherein the step of slowing addition of the alkaline solution is carried out to the extent that about 3% or less excess alkali is added to the solution.

4. Process of claim 3 wherein the crude MBT is added in a molten state, the alkali is sodium hydroxide, and concentration of MBT is about 10 to 35% by weight after all ingredients are added to the reactor.

5. Process of claim 4 wherein the solvent treatment is accomplished by passing the salt solution countercurrently to the solvent in a column and taking off the solvent phase from the top of the column and the salt solution from the bottom of the column, the process further including the steps of diluting the salt solution with about ½ to 2 volumes of water, agitating the resulting solution until solid impurities drop out, and filtering out solid impurities therefrom.

6. Process of claim 3 including the step of treating the salt solution following the solvent treatment with pure oxygen while agitating the solution.

7. Process of claim 3 including the step of treating the salt solution following the solvent treatment with pressurized gas selected from air and pure oxygen, the gas treatment being accomplished by introducing the gas into a closed vessel containing the salt solution and vigorously agitating the solution.

8. Process of claim 7 wherein the gas is added to the vessel to the extent of creating above-atmospheric pressure in the vessel and agitation is sufficiently vigorous to result in a substantially constant high initial oxygen uptake by the solution.

9. Process of claim 8 wherein the gas is oxygen and wherein agitation is continued until oxygen uptake drops substantially or stops entirely, initial pressure in the vessel being on the order of 50 to 500 psig.

10. In a process for purification of crude 2-mercaptobenzothiazole (MBT) obtained by the reaction of aniline, carbon disulfide, and sulfur at a high temperature and under an elevated pressure which comprises dissolving crude MBT in an aqueous alkaline solution in a reactor by adding the alkaline solution to the crude MBT, agitating contents of the reactor until essentially all MBT is converted to the MBT salt, treating the salt solution with a solvent that solubilizes certain of the impurities, and separating the salt solution from the solvent having dissolved therein certain of the impurities, the improvement comprising treating the salt solution following the solvent treatment with pure oxygen while agitating the solution, the process further including the steps of measuring pH of the salt solution when addition of the alkaline solution is made during which time an abrupt rise in pH takes place that follows a period of gradual pH increase, and stopping addition of the alkaline solution in response to the abrupt rise in pH.

11. Process of claim 10 including the step of slowing addition of the alkaline solution before the abrupt rise in pH is reached to minimize addition of excess alkali to the solution, the abrupt rise being characterized by a rise of at least one-quarter of one pH point during addition of less than about 3% of the alkali.

12. Process of claim 11 wherein the step of slowing addition of the alkaline solution is carried out to the extent that about 5% or less excess alkali is added to the solution.

* * * * *